(12) United States Patent
Harding et al.

(10) Patent No.: US 6,380,226 B1
(45) Date of Patent: Apr. 30, 2002

(54) SALTS OF AN ANTI-MIGRAINE INDOLE DERIVATIVES

(75) Inventors: Valerie Denise Harding; Ross James Macrae; Ronald James Ogilvie, all of Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/596,017

(22) Filed: Jun. 15, 2000

Related U.S. Application Data

(62) Division of application No. 08/776,680, filed as application No. PCT/EP95/01914 on May 17, 1995, now Pat. No. 6,110,940.

(30) Foreign Application Priority Data

Aug. 27, 1994 (GB) ............................... 9417310

(51) Int. Cl.[7] ...................... A61K 31/41; A61K 31/425; C07D 271/06; C07D 417/00; C07D 209/02
(52) U.S. Cl. ...................... 514/364; 514/365; 514/323; 548/131; 548/181; 548/468
(58) Field of Search ................. 514/364, 365, 514/323; 548/131, 181, 468

(56) References Cited

U.S. PATENT DOCUMENTS

| | | | |
|---|---|---|---|
| 2,773,875 A | 12/1956 | Finkelstein | 548/466 |
| 3,037,031 A | 5/1962 | Lewis et al. | 548/466 |
| 4,252,803 A | 2/1981 | Webb | 424/248.5 |
| 4,803,218 A | 2/1989 | Stanley et al. | 548/466 |
| 4,855,314 A | 8/1989 | Oxford et al. | 514/415 |
| 5,208,248 A | 5/1993 | Baker et al. | 514/364 |
| 5,348,968 A | 9/1994 | Lavielle | 548/468 X |
| 5,409,941 A | 4/1995 | Nowakowski | 514/33 |
| 5,498,626 A | 3/1996 | Macor | 514/414 |
| 5,545,644 A | 8/1996 | Macor et al. | 514/323 |
| 5,559,129 A | 9/1996 | Macor et al. | 514/323 |
| 5,559,246 A | 9/1996 | Macor et al. | 514/468 |
| 5,578,612 A | 11/1996 | Macor et al. | 514/323 |
| 5,594,014 A | 1/1997 | Macor et al. | 514/364 |

FOREIGN PATENT DOCUMENTS

| | | |
|---|---|---|
| EP | 465398 | 1/1992 |
| EP | 497512 | 8/1992 |
| GB | 851780 | 10/1960 |
| GB | 886684 | 1/1962 |
| GB | 893707 | 4/1962 |
| GB | 966562 | 8/1964 |
| GB | 2081717 | 2/1982 |
| NL | 74527 | 4/1954 |
| NL | 74786 | 5/1954 |
| WO | 9206973 | 4/1992 |
| WO | 9311106 | 6/1993 |
| WO | 9314087 | 7/1993 |
| WO | 9318032 | 9/1993 |
| WO | 9320073 | 10/1993 |
| WO | 9321177 | 10/1993 |
| WO | 9321178 | 10/1993 |
| WO | 9321180 | 10/1993 |
| WO | 9323396 | 11/1993 |
| WO | 9424127 | 10/1994 |
| WO | 9425023 | 11/1994 |
| WO | 9506636 | 3/1995 |

OTHER PUBLICATIONS

Bader, et al., *J. Am. Chem. Soc.*, 79, 5686–5689 (1957).
Gray, *J. Org. Chem.*, 23, 1453–1454 (1958).
Moore, et al., *J. Org. Chem.*, 29, 2860–2864 (1964).
Cain, et al., *J. Am. Chem. Soc.*, 105 908, 911, 912, (1983).
Markowitz, et al. *J. Neurosci.*, 7 (12) 4736 (1987).
Lee, et al., *Brain Res.*, 626, 303–305 (1993).
P.P.A. Humphrey, et al., *Br. J. Pharmacol.*, 94, 1128 (1988).
W. Feniuk, et al., *Br. J. Pharmacol.*, 96, 83 (1989).
Reagent for Org. Syn, 1, 112 (1967).
Mohr, et al., *Tetrahedron*, 38(1), 147–152 (1982).
Friderichs, et al., *Chem. Ab.*, 83, 28056 (1975).
Kiyooka, et al., *J. Org. Chem.*, 5409 (1989).
Hamada, et al., *Chem. Pharm. Bull.*, 1921 (1982).
Lee, et al., *Soc. Neurosci* Nov. 1993 Meeting 19 (Part 2), #565.6.
Moskowitz, *7th World Congress on Pain* Aug. 1993, #667.
Leonard, et al., *Neuropham.*, 11, 373–384 (1972).

*Primary Examiner*—Richard L. Raymond
*Assistant Examiner*—Tamthom N. Truong
(74) *Attorney, Agent, or Firm*—Peter C. Richardson; Paul H. Ginsburg; A. David Joran

(57) ABSTRACT

A crystalline, β-polymorphic form of a compound of formula (I):

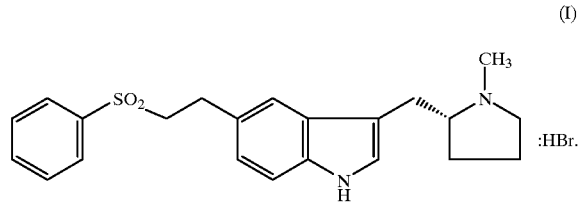

10 Claims, 6 Drawing Sheets

SALTS OF AN ANTI-MIGRAINE INDOLE DERIVATIVES

This application is a Div. of Ser. No. 08/776,680 filed Feb. 2, 1997 U.S. Pat. No. 6,110,940 which is a 371 of PCT/EP95/01914 filed May 17, 1995.

The present invention relates to hydrobromide salts of 3-(N-methyl-2(R)-pyrrolidinylmethyl)-5-(2-phenytsulphonylethyl)-1H-indole having the formula (I):

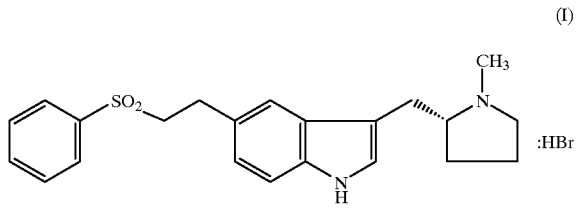

(I)

In a preferred aspect, the invention relates to a particular polymorphic form, hereinafter referred to as the α-form, of the hydrobromide salt identified above. In addition it relates to an intermediate polymorphic form, hereinafter referred to as the β-form, of the said hydrobromide salt, to processes for the preparation of the α- and β-forms, to pharmaceutical compositions containing the α-form, and to uses of the α-form in medicine.

WO-A-92/06973 relates to a series of 3,5disubstituted indoles and pharmaceutically acceptable salts thereof useful in the treatment of migraine and other disorders. Examples cited therein of such salts are the hydrochloride, hydrobromide, hydroiodide, nitrate, sulphate or bisulphate, phosphate or acid phosphate, acetate, lactate, citrate or acid citrate, tartrate or bitartrate, succinate, maleate, fumarate, gluconate, saccharate, benzoate, methanesulphonate and pamoate. Specifically disclosed therein is 3-(N-methyl-2 (R)-pyrrolidinylmethyl)-5(2-phenylsulphonylethyl)-1H-indole and its hemisuocinate salt, the latter being characterised as a non-crystalline foam. Further studies have confirmed that this salt is unsuitable for pharmaceutical formulation, as numerous attempts to obtain it in a form which has the properties required for formulation have been unsuccessful.

Thus the problem addressed by the present invention is the provision of a pharmaceutically acceptable salt of 3-(N-methyl-2(R)-pyrrolidinylmethyl)-5(2-phenylsulphonylethyl)-1H-indole which can be efficiently processed to provide stable and effective formulations of the drug, in particular solid and compressible dosage forms. Such dosage forms include conventional-release oral tablets, controlled-release (matrix) tablets, fast-dissolving tablets (e.g. freeze-dried), sublingual tablets, buccal tablets, oral powder- and granule-filled capsules, powders for reconstituted suspensions, conventional and controlled-release multiparticulate systems filled into capsules or compressed into tablets, lozenges, dragees, suppositories, pessaries, solid implants, lyophile plugs, nanoparticles and microparticles and powder for suspension and nasal delivery, and dry inhalation systems.

Important criteria to be satisfied are, inter alia, that the selected salt should be crystalline, of suitable melting point, non-hygroscopic, compressible and possess solid-state stability, coupled with acceptable solubility and dissolution behaviour.

This problem has been solved by the surprising finding of a novel α-form of the hydrobromide salt of formula (I) which meets the above requirements; thus it is proeminently suitable for providing pharmaceutical formulations in solid dosage form, in particular for oral, buccal and sublingual administration.

The first step in approaching the solution to the problem was the generation of an acid addition salt of the monoacidic base, 3-(N-methyl-2(R)-pyrrolidinylmethyl)-5-(2-phenylsulphonylethyl)-1H-indole, which is both crystalline and of high enough melting point (>ca. 130° C.) to have the potential to undergo pharmaceutical processing during solid dosage form manufacture and compaction.

Attempts were made to obtain a suitable form of the following salts: hydrochloride, hydrobromide, hemisulphate, bisulphate, nitrate, acid phosphate, phosphate, methanesulphonate, benzenesulphonate, p-toluenesulphonate, (+)-camphorsulphonate, acetate, benzoate, citrate, hemifumarate, fumarate, hemimaleate, maleate, hemisuccinate, succinate, hemi-L-tartrate, L-tartrate, hemi-D-tartrate, D-tanrate, L-lactate, (R)-(−)-mandelate, hippurate, hemiphthalate, phthalate and hemi-terephthalate.

Of these thirty possible salts, only four could be obtained as crystalline solids, namely the hemisulphate, hydrochloride, hydrobromide and benzenesulphonate; the remainder were obtained as non-crystalline/low or non-sharp melting/sticky solids, gums, glasses, froths, resins or oils. Moreover, of the four crystalline salts, the benzenesulphonate proved to have an insufficiently high melting point (m.p.) of 74–75° C. Thus only the hemisulphate, hydrochloride and hydrobromide salts were progressed to more detailed studies.

Hemisulphate Salt

The hemisulphate salt initially isolated (m.p. 145–147° C.), designated the β-form, does not show a clean single-melting endotherm when examined by differential scanning calorimetry (DSC) but rather a complex trace indicative of polymorphic transition. Indeed, this β-form is very hygroscopic at relative humidities (RH) higher than 50% and, under certain conditions, water uptake can cause polymorphic conversion to an alternative form, designated the α-form, of m.p. 185° C., or even degradation. Furthermore, the β-form undergoes a colour change on compression and causes punch-filming during tabletting and thus, for a variety of reasons, its physicochemical properties render it unsuitable for the development of solid dosage forms.

Whilst the α-form of the hemisulphate salt does not display solid state instability associated with water uptake, it is extremely hygroscopic nevertheless and therefore also unsuitable for development because of consequential difficulties with variable flow properties, and bulk and dosage form instability which precludes, inter alia, accurate assignment of drug activity.

Hydrochloride Salt

Depending on the solvent used as reaction medium and for crystallisation, either of two forms of the hydrochloride salt can be obtained. The first of these to be isolated and characterised, designated the β-form, of m.p. 125–129° C. (broad endotherm at 135° C. at a scan rate of 20° C./min. by DSC, but no dehydration endotherms apparent), was found to have a water content of 4.42% (1.08 mol) by Karl Fischer titrimetry (KFT). However, although hygroscopicity studies revealed that the β-form does not display solid state instability, it was excluded from further development by its behaviour during compression studies in which melting and sticking of the disk to the punches were observed, thus reinforcing the requirement for a higher melting solid.

The alternative hydrochloride salt, designated the α-form, showed a major, sharp endotherm at 165° C. by DSC (scan rate 20° C./min.). Determination of its hygroscopicity profile revealed that after seven days at a temperature (T) of 40° C. and RH of 75%, unlike the β-form, a significant amount of water had been taken up. This water uptake was found to be associated with changes in the DSC trace which demonstrated that, at least under these humidity conditions, the anhydrous α-form converts to the hydrated β-form. Thus pharmaceutical development of the α-form is also precluded by inadequate physical stability.

Hydrobromide Salt

The hydrobromide salt is also isolable in one of two forms, depending on the preparative conditions employed. The lower melting form, designated the β-form, was found not to be a viable option for the development of a solid dosage form because, when attempts are made to improve its quality, it undergoes polymorphic conversion to a higher melting form, designated the α-form.

However, by contrast, the novel α-form of the hydrobromide salt of formula (I) was found to be unique in unexpectedly possessing the combination of properties required to enable the efficient development of solid dosage forms, namely those of crystallinity, sufficiently high m.p., lack of hygroscopicity, solid-state stability, compressibility and lack of polymorphic conversion, together with satisfactory solubility and dissolution rate profiles.

The present invention therefore provides a crystalline, polymorphic α-form of a hydrobromide salt of formula (I), whose infra-red (IR) spectrum as a mull in nujol shows significant absorption bands at ν=3371, 3293, 2713, 2524, 1419, 1343, 1307, 1264, 1151, 1086, 1020, 1008, 999, 922, 900, 805, 758, 740, 728, 689, 672, 652, 640, 598, 581, 573, 531, 498, 465, 457, 443, 428, 422, 414 and 399 cm$^{-1}$.

The α-form is further characterised by its powder X-ray diffraction (PXRD) pattern obtained using copper radiation filtered with a graphite monochromator (λ=0.15405 nm) which shows main peaks at 9.7, 10.7, 15.9, 16.5, 17.8, 18.3, 19.3, 19.8, 20.1, 21.2, 24.4, 25.5, 25.8, 26.7, 27.6 and 29.4 degrees 2θ.

The α-form is yet further characterised by its differential scanning calorimetry (DSC) trace which shows a sharp endotherm at 176.5° C. at a scan rate of 20° C./min.

The invention also provides a crystalline, polymorphic β-form of a hydrobromide salt of formula (I), which can be used as an intermediate in the preparation of the α-form. Its IR spectrum as a mull in nujol shows significant absorption bands at ν=3239, 2672, 2656, 2632, 1409, 1366, 1351, 1334, 1303, 1293, 1152, 1138, 1122, 1098, 1086, 791, 771, 746, 688, 634, 557, 528, 484, 476, 469, 463, 455, 432, 424, 413 and 401 cm$^{-1}$.

The β-form is further characterised by its PXRD pattern obtained using copper radiation filtered with a graphite monochromator (λ=0.15405 nm) which shows main peaks at 11.0, 17.2, 19.2, 20.1, 21.6, 22.6, 23.6 and 24.8 degrees 2θ.

The β-form is yet further characterised by its DSC trace which shows a sharp endotherm at 154.8° C. at a scan rate of 20° C./min.

The invention further provides processes for the preparation of the α-form of a compound of formula (I), as illustrated by the following.

(A)

Treatment of a solution of 3-(N-methyl-2(R)-pyrrolidinylmethyl)-5-(2phenylsulphonylethyl)-1H-indole in a suitable solvent, preferably acetone, at room temperature, with an aqueous solution of hydrogen bromide, followed by crystallisation of the isolated crude oil from a suitable solvent, preferably 2-propanol, affords the α-form of the required hydrobromide salt.

(B)

Treatment of a solution of 3-(N-methyl-2(R)-pyrrolidinylmethyl)-5-(2-phenylsulphonylethyl)-1H-indole in a suitable solvent, preferably acetone or an ether solvent such as tetrahydrofuran or 1,2-dimethoxyethane, more preferably 1,2-dimethoxyethane, at from 0 to 10° C., with an aqueous solution of hydrogen bromide, furnishes the β-form of the required hydrobromide salt.

Crystallisation of the β-form from a suitable solvent, preferably aqueous acetone, followed by slurrying of the resulting mixture, gives the desired α-form.

(C)

Treatment of a solution of 3N-methyl-2(R)-pyrrolidinylmethyl)-5-(2-phenylsulphonylethyl)-1H-indole in a suitable solvent, preferably acetone, at from 0 to 5° C. with an aqueous solution of hydrogen bromide and then slurrying of the reaction mixture, optionally followed by heating under reflux, cooling and further slurrying, provides the required α-form.

As previously mentioned, WO-A-92/06973 discloses 3(N-methyl-2(R)-pyrrolidinylmethyl)-5-(2-phenylsulphonylethyl)-1H-indole and pharmaceutically acceptable salts thereof for the treatment of migraine and other disorders (incorporated herein by reference). Thus the present invention also relates to pharmaceutical compositions containing the α-form of the hydrobromide salt thereof, uses of the α-form as a medicament and for the manufacture of a medicament for the treatment of migraine and said other disorders, and a method of treating a mammal having migraine or any of said other disorders with the α-form.

The in vitro evaluation of the peripheral 5-HT, receptor agonist activity of the α-form can be carried out by testing the extent to which it mimics sumatriptan in contracting the isolated dog saphenous vein strip (P. P. A. Humphrey et al., Brit. J. Pharmacol., 1988, 94, 1123). This effect can be blocked by methiothepin, a known 5-HT antagonist. Sumatriptan is known to be useful in the treatment of migraine and produces a selective increase in carotid vascular resistance in the anaesthetized dog and a consequent decrease in carotid arterial blood flow. It has been suggested (W. Feniuk et al., Brit. J. Pharmacol., 1989, 96, 83) that this is the basis of its efficacy.

The central 5-HT, agonist activity of the α-form can be measured in in vitro receptor binding assays as described for the 5-HT$_{1A}$ receptor, using rat cortex as the receptor source and [$^3$H]8-OH-DPAT as the radioligand (D. Hoyer et al., Europ. J. Pharmacol., 1985, 118, 13), and as described for the 5-HT$_{1D}$ receptor, using bovine caudate as the receptor source and [$^3$H]5-HT as the radioligand (R. E. Heuring and S. J. Peroutka, J. Neuroscience, 1987, 7, 894).

In therapy, the α-form of the hydrobromide salt of formula (I) can be administered alone, but will generally be administered in admixture with pharmaceutically acceptable excipients, including glidants, disintegrants and lubricants, selected with regard to the intended route of administration and standard pharmaceutical practice. In particular, it may be administered orally in the form of tablets, dragees or lozenges containing excipients such as starch or lactose, or in capsules, ovules or implants, either alone or in admixture with excipients. For buccal or sublingual administration, it may be administered in the form of tablets, dragees or lozenges which can be formulated in a conventional manner.

For oral, buccal or sublingual administration to patients, the daily dosage level of the α-form of the salt of formula (I) will be from 0.01 mg to 20 mg/Kg (in single or divided doses). Thus tablets or capsules will contain from 0.5 mg to 0.5 g of active compound for administration singly, or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Thus the invention provides a pharmaceutical composition comprising the α-form of a compound of formula (I) together with a pharmaceutically acceptable diluent or carrier.

The invention also provides the α-form of a compound of formula (I), or a pharmaceutical composition thereof, for use as a medicament.

The invention further includes the use of the α-form of a compound of formula (I), or a pharmaceutical composition thereof, both for the manufacture of a medicament for the curative or prophylactic treatment of migraine or an associated condition such as cluster headache, chronic paroxysmal hemicrania or headache associated with a vascular disorder, or of depression, anxiety, an eating disorder, obesity, drug abuse, hypertension or emesis, and also for the manufacture of a medicament for the curative or prophylactic treatment of a medical condition for which a selective agonist of $5-HT_1$ receptors is indicated.

In a further aspect, the invention provides both a method of treating a human being to cure or prevent migraine or an associated condition such as cluster headache, chronic paroxysmal hemicrania or headache associated with a vascular disorder, or depression, anxiety, an eating disorder, obesity, drug abuse, hypertension or emesis, and also a method of treating a human being to cure or prevent a medical condition for which a selective agonist of $5-HT_1$ receptors is indicated, which comprises administering to said human being an effective amount of the α-form of a compound of formula (I), or a pharmaceutical composition thereof.

The preparation of the α-form of the hydrobromide salt of formula (I) and pharmaceutical compositions thereof are illustrated by the following Examples.

Room temperature means 20 to 25° C. and m.p. means melting point.

IR means infra red, PXRD means powder X-ray diffraction, DSC means differential scanning calorimetry, T means temperature, RH means relative humidity, HPLC means high performance liquid chromatography, KFT means Karl Fischer titrimetry.

EXAMPLE 1

3-(N-Methyl-2(R)-pyrrolidinylmethyl)-5-(2-phenylsulphonylethly)-1H-indole hydrobromide, α-form 49% w/w Hydrobromic acid (432 mg, 0.3 ml, 2.6 mmol) was added to a stirred solution of 3-(N-methyl-2(R)-pyrrolidinylmethyl)-5-(2-phenylsulphonylethyl)-1H-indole (1.0 g, 2.6 mmol) in acetone (10 ml) at room temperature. After a further 15 minutes, the reaction mixture was evaporated under reduced pressure to give a yellow liquid; the residual water therein was then azeotropically removed using 2-propanol. The resulting cloudy, yellowish oil (1.55 g) was triturated with ether and then dissolved in hot 2-propanol (25 ml); this solution, on cooling, provided the title compound (1.13 g) as a pale yellow crystalline solid after filtration, washing with 2-propanol and drying in vacuo, m.p. 165–170° C. Found: C,56.67; H,5.78; N,5.82. $C_{22}H_{26}N_2O_2S$; HBr requires C,57.02; H,5.87; N,6.04%.

EXAMPLE 2

3-(N-Methyl-2(R)-pyrrolidinylmethyl)-5-(2-phenylsulphonylethyl)-1H-indole hydrobromide, α-form (a) 3-N-Methyl-2(R)-pyrrolidinylmethyl)-5-(2-phenylsulphonylethyl)-1H-indole hydrobromide, β-form 49% w/w Hydrobromic acid (27.86 ml, 0.25 mol) was added over 1 hour to a stirred solution of 3N-methyl-2(R)-pyrrolidinylmethyl)-5-(2-phenylsulphonylethyl)-1H-indole (92.86 g, 0.24 mol) in 1,2-dimethoxyethane (2.08 l) at about 5° C. The cooling bath was removed and the resulting slurry was allowed to granulate by stirring at room temperature for a further 18 hours. Filtration, followed by washing with 1,2-dimethoxyethane and drying in vacuo, afforded the required product (97.9 g) as a solid, m.p. 150–151° C. Found: C,56.77; H,5.87; N,5.85. $C_{22}H_{26}N_2O_2S$; HBr requires C,57.02; H,5.87; N,6.04%.

(b)

A stirred mixture of the previous product (20 g), acetone (140 ml) and water (6 ml) was heated under reflux until complete dissolution of the β-form was achieved. The solution was then allowed to cool to room temperature, stirred for 1 hour and then acetone (460 ml) added to the resulting slurry. After a further 1 hour, the slurry was cooled to 0–5° C. and stirring continued for up to 18 hours. The colourless, crystalline solid was collected by filtration, washed with acetone and dried in vacuo to furnish the title compound (13.22 g), which was identical to that of Example 1.

EXAMPLE 3

3-(N-Methyl-2(R)-pyrrolidinylmethyl)-5-(2-phenylsulohonylethyl)-1H-indole hydrobromide, α-form 62% w/w Hydrobromic acid (1.706 g, 13.07 mmol) was added over 1 hour to a stirred solution of 3-(N-methyl-2(R)-pyrrolidinylmethyl)-5-(2-phenylsulphonylethyl)-1H-indole (5.0 g, 13.07 mmol) in acetone (112 ml) at 0–5° C. After slurrying of the reaction mixture at 0–5° C. for 3 hours, heating under reflux for 2 hours was effected followed by cooling to 0–5° C. and further slurrying for 1 hour at this temperature. Filtration, followed by washing with acetone and drying in vacuo, furnished the title compound (5.18 g), which was identical to that of Example 1.

In Examples 4 to 6, "active ingredient" means the α-form of the hydrobromide salt

EXAMPLE 4

Tablets for Oral Administration

| A. Direct Compression | | |
|---|---|---|
|  | mg/tablet | for 50 g mix |
| Active ingredient | 12.12 | 6.06 g |
| Microcrystalline cellulose Ph Eur | 25.00 | 12.50 g |

-continued

A. Direct Compression

|  | mg/tablet | for 50 g mix |
|---|---|---|
| Lactose Ph Eur | 60.88 | 30.44 g |
| Croscarmellose sodium NF | 1.00 | 0.50 g |
| Magnesium stearate Ph Eur | 1.00 | 0.50 g |

The active ingredient is sieved and blended with the other components. The resultant mix is compressed into tablets using a rotary tablet press (Manesty Betapress) fitted with 6 mm normal concave punches. The resultant tablets can be film coated with an appropriate film coating material.

B. Wet Granulation

|  | mg/tablet | for 50 g mix |
|---|---|---|
| Active ingredient | 1.21 | 0.76 g |
| Lactose Ph Eur | 56.03 | 35.02 g |
| Maize starch Ph Eur | 18.68 | 11.67 g |
| Polyvinylpyrrolidone (2% w/v soln) | 1.60 | 1.00 g |
| Colloidal anhydrous silica Ph Eur | 0.08 | 0.05 g |
| Croscarmellose sodium NF | 1.60 | 1.00 g |
| Magnesium stearate Ph Eur | 0.80 | 0.50 g |

The polyvinylpyrrolidone is dissolved in purified water to an appropriate concentration. The active ingredient is sieved and blended with all of the other components except the magnesium stearate. Suitable volumes of the polyvinylpyrrolidone solution are added and the powders are granulated. After drying, the granules are screened and blended with the magnesium stearate. The granules are then compressed into tablets using suitable diameter punches.

Tablets of other strengths may be prepared by altering the ratio of active ingredient to excipients or the compression weight and using punches to suit.

EXAMPLE 5

Capsules

|  | mg/capsule |
|---|---|
| Active ingredient | 18.18 |
| Lactose Ph Eur | 208.89 |
| Maize starch Ph Eur | 69.63 |
| Colloidal anhydrous silica Ph Eur | 0.30 |
| Magnesium stearate Ph Eur | 3.00 |
| Fill weight | 300.00 |

The active ingredient is sieved and blended with the other components. The mix is filled into size No 2 hard gelatin capsules using suitable machinery. Other doses may be prepared by altering the fill weight and, if necessary, changing the capsule size to suit.

EXAMPLE 6

Sublingual Tablets

|  | mg/tablet | for 50 g mix |
|---|---|---|
| Active ingredient | 1.2 | 0.750 g |
| Lactose Ph Eur | 25.0 | 15.625 g |
| Maize starch Ph Eur | 25.0 | 15.625 g |
| Mannitol Ph Eur | 25.0 | 15.625 g |
| Croscarmellose sodium NF | 3.0 | 1.875 g |
| Magnesium stearate Ph Eur | 0.8 | 0.500 g |

The active ingredient is sieved through a suitable sieve, blended with the excipients and compressed using suitable punches. Tablets of other strengths may be prepared by altering either the ratio of active ingredients to excipients or the compression weight and using punches to suit.

BRIEF DESCRIPTION OF THE DRAWINGS

Characterisation of the hydrobromide Salt α- and β-forms by IR, PXRD and DSC analysis
(a) IR Spectroscopy
The IR spectra were determined over the wave number (ν) range 4000 to 400 cm$^{-1}$ as nujol mulls using a Nicolet 800 FT-IR spectrometer and are represented by FIGS. 1A and 1B. For identification of the ν of significant absorption bands, vide supra. ps (b) PXRD
The PXRD patterns were obtained using a Siemens D500 diffractometer which was operated at 40 kV/30 mA and using copper radiation filtered with a graphite monochromator (λ=0.15405 nm) and a scintillation counter detector. For each form, beam intensity as a function of the angle 2θ was recorded over the range 2° to 45° 2θ using a step scan mode counting for six seconds at step intervals of 0.03° 2θ. For identification of the main peaks (degree 2θ) seen in each pattern, represented by FIGS. 2A and 2B, vide supra.
(c) DSC
Samples (ca 5 mg) of each form were analysed using a Perkin-Elmer 7 Series thermal analyser at a scanning rate of 20° C. per minute. For identification of the respective endotherms, shown in the representative DSC thermograms of FIGS. 3A and 3B, vide supra.
Hygroscopicity/Solid State Stability Studies Samples (ca 10 mg) were sieved (250 μm) and then stored at each of the following conditions of temperature (T) and relative humidity (RH) for up to 4 weeks:
30° C. at II, 75 and 90% RH and
40° C. at II, 75 and 90% RH,
the required humidities being achieved using the appropriate saturated salt solution in a dessicator. Measurements of water content changes were conducted by weight analysis using a microbalance and by Karl Fischer titrimetry (KFT), and chemical and physical stability evaluation by high performance liquid chromatography (HPLC) and DSC.
HPLC analyses were performed on a LDC isocratic system under the following conditions:
column—Novapak $C_{18}$, 5μm, 15 cm; mobile phase—pH 6.0, 60:40 v/v 0.02M $KH_2PO_4$ (0.5% triethylamine): methanol; detection—UV (254 nm); flow rate—1.0 ml/min; injection volume —20 μl; sample 0.1 mg/ml in mobile phase.
KFT was performed using a Mitsubishi moisturemeter and ca 10 mg of each sample.
Table 1 shows hygroscopicity results for the α-form of the hydrobromide salt and the α- and β-reforms of the hemisulphate salt, expressed as moisture changes determined by % weight change under various conditions of T(°C) and RH(%).

It can be seen from Table 1 that the α-form of the hydrobromide salt showed relatively stable weights throughout the course of the study, with slight loss of moisture at low (11%) RH being observed at both 30 and 40° C., and these results were corroborated by those obtained by KFT analysis. Particularly noteworthy is that little change in its moisture content was noted at a RH of 75%, by comparison with the significant uptake seen at 40° C. for both the β-form and, especially, the α-form of the hemisulphate salt. Moreover, water uptake by the β-form of the hemisulphate salt was accompanied by a change in colour of the sample from cream to yellow; although the α-form of the hemisulphate salt absorbed water even more rapidly than the β-form, no concomitant colour

TABLE 1

Figure 1A:
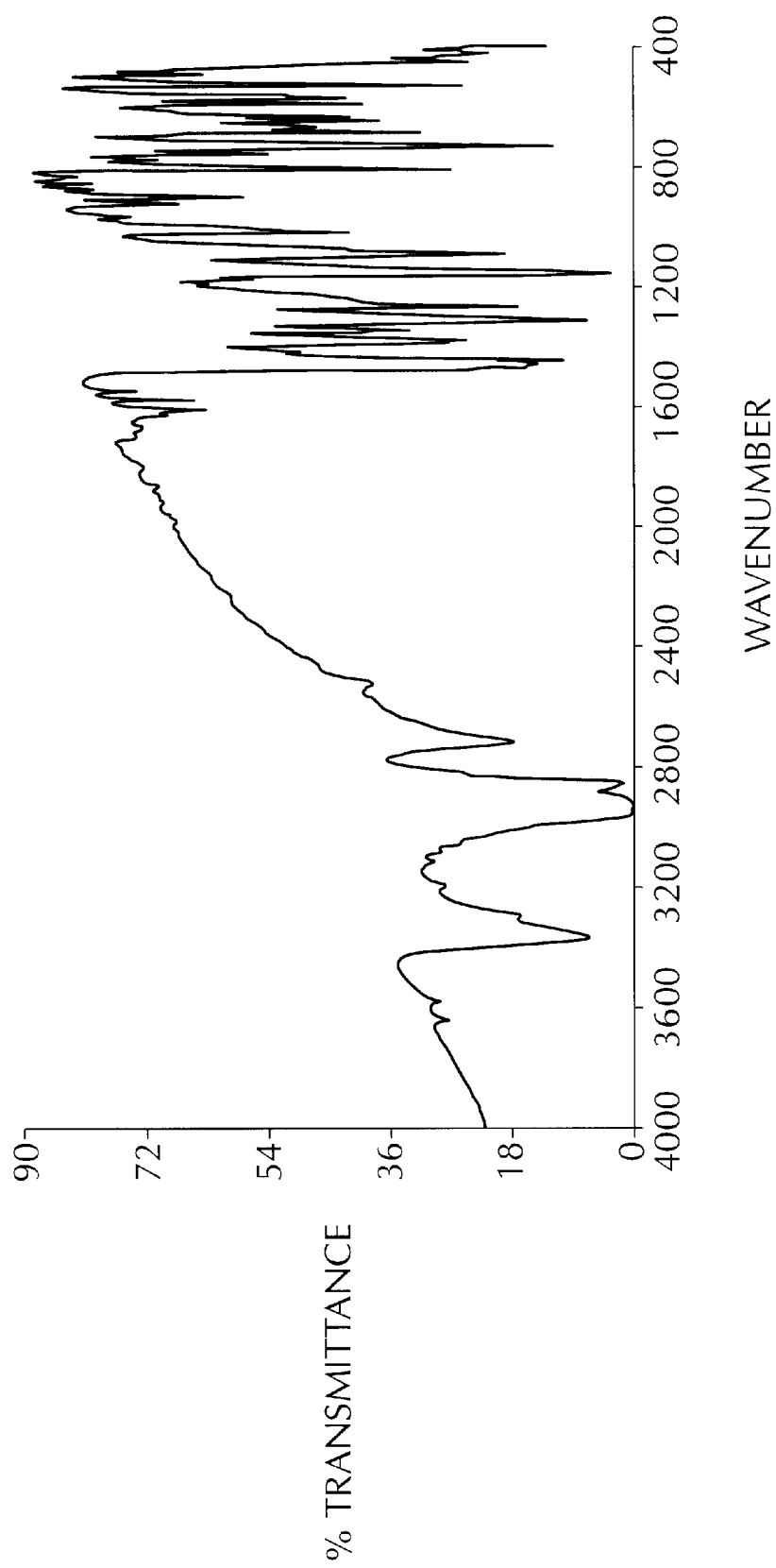
Figure 1B:
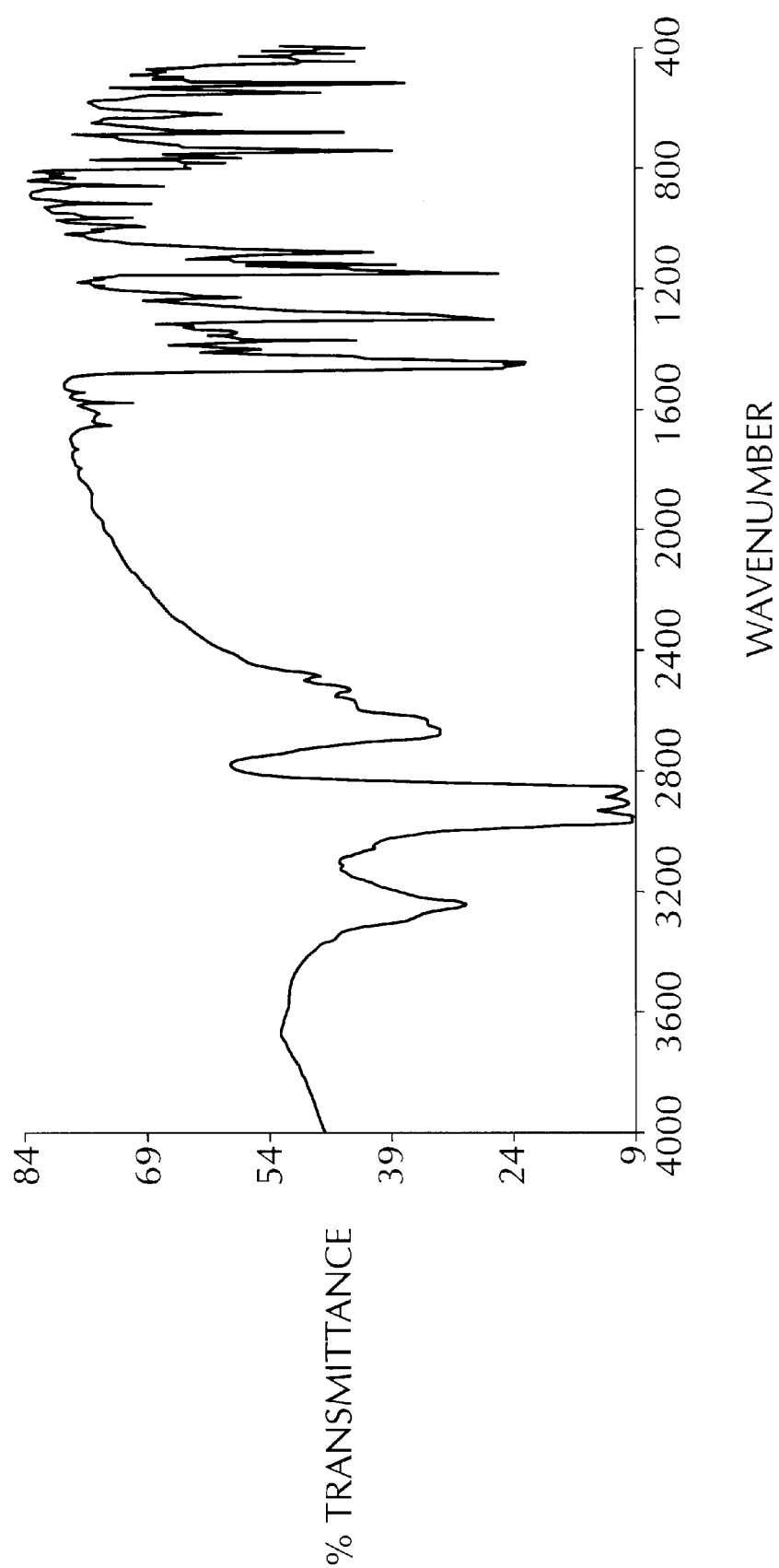
Figure 2A:
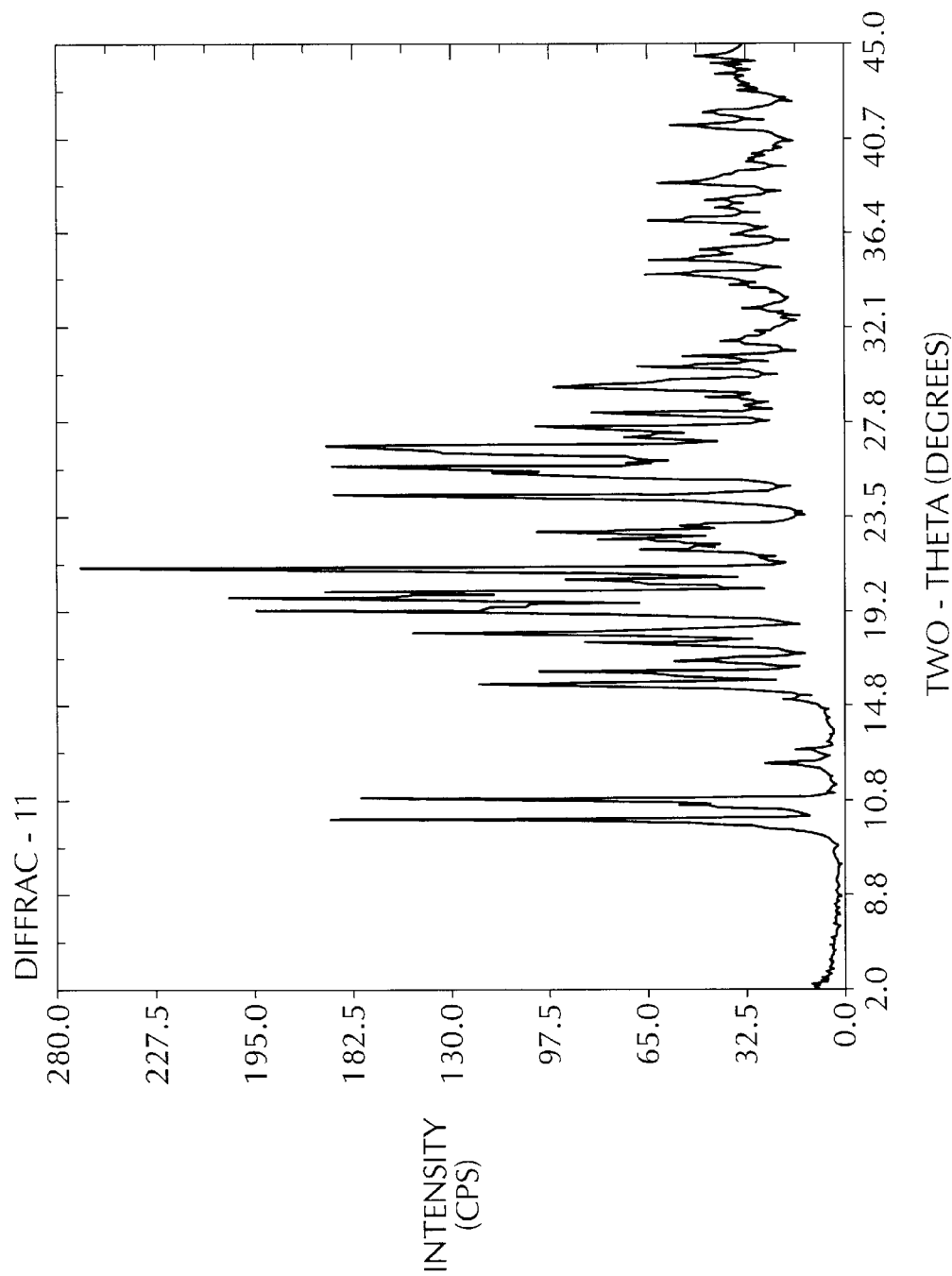
Figure 2B:
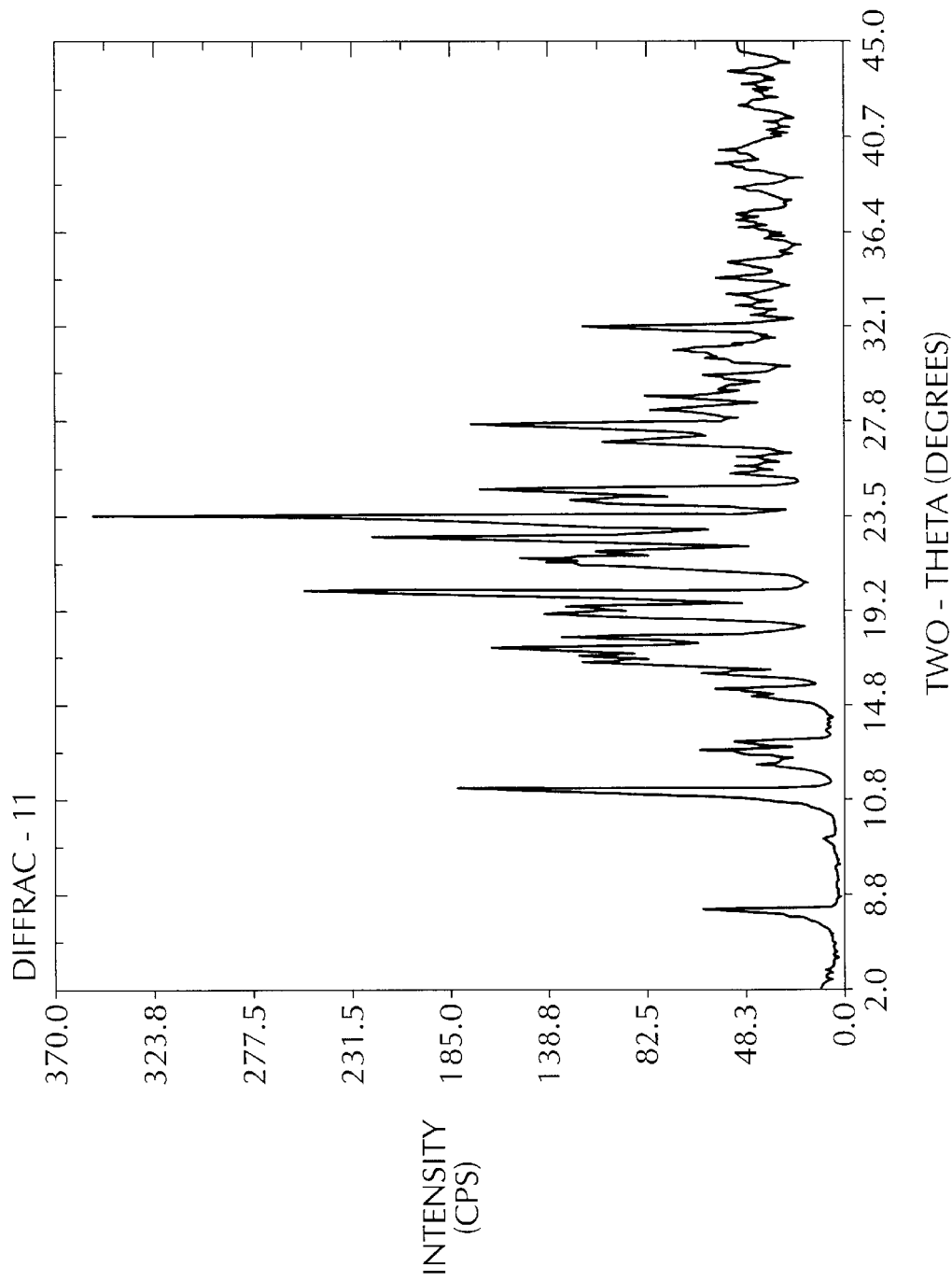
Figure 3A:
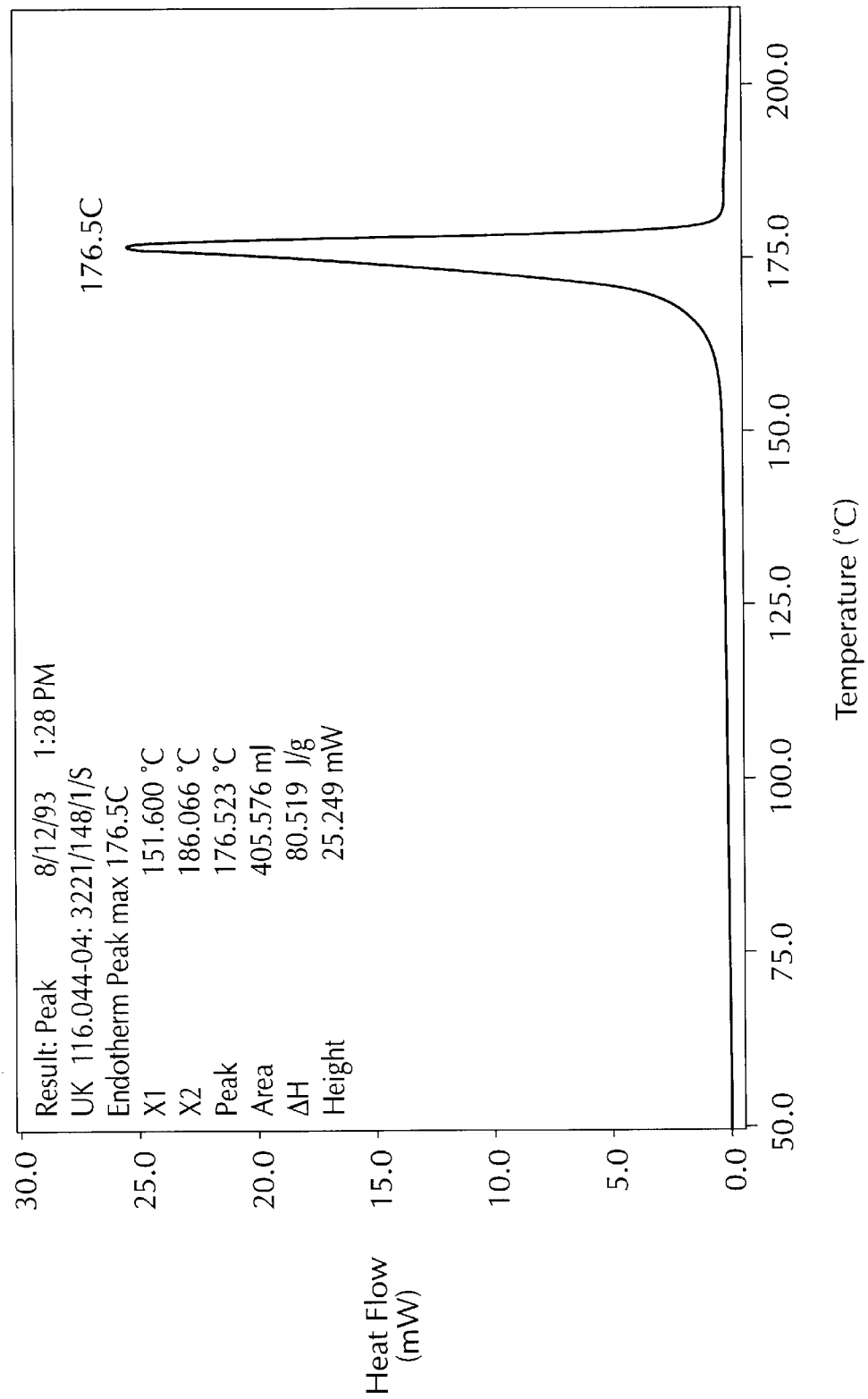
Figure 3B:
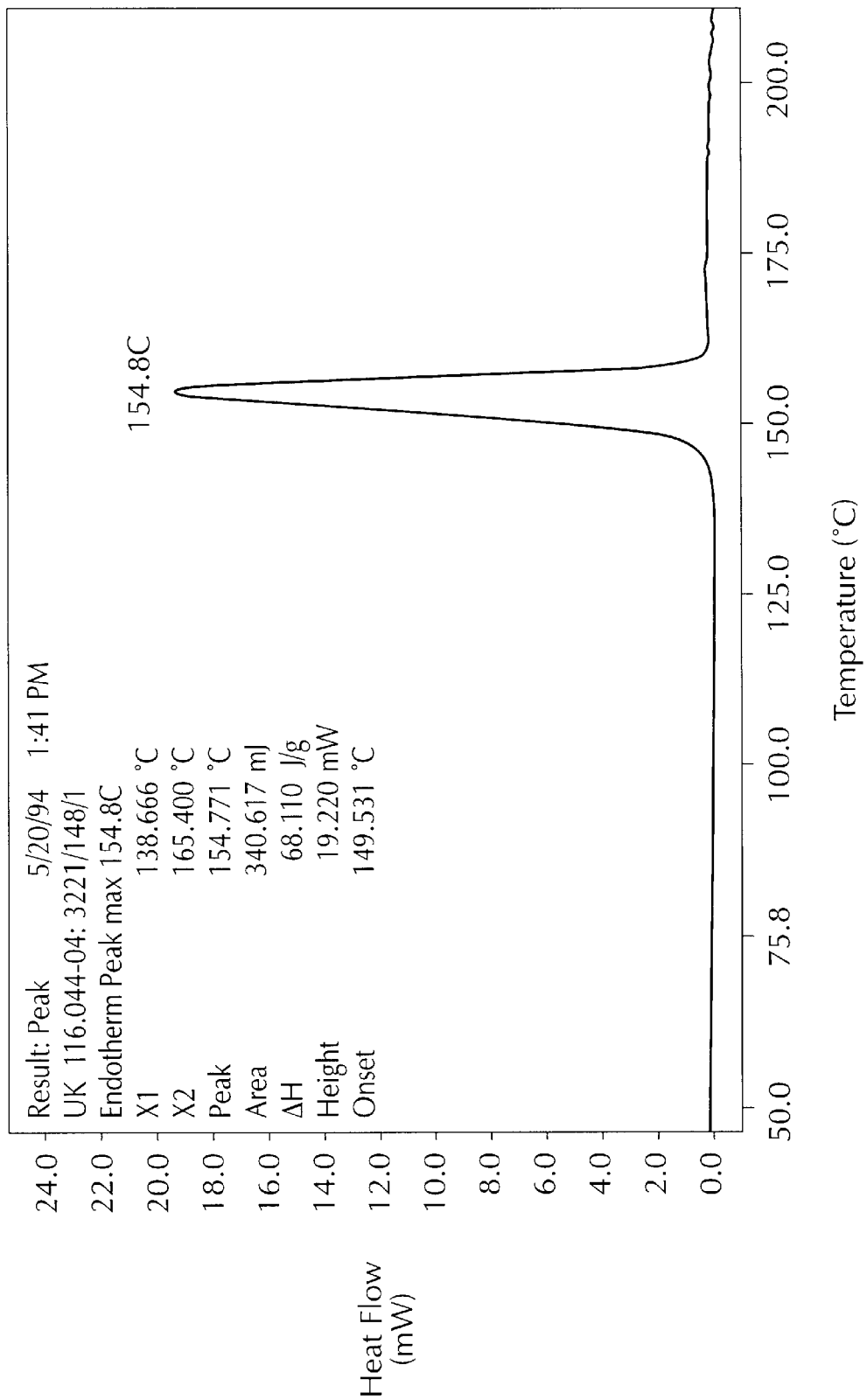

| SALT FORM | T/RH | Week 1 | Week 2 | Week 3 | Week 4 |
|---|---|---|---|---|---|
| α-HBr | 30/11 | −0.45 | −0.51 | +0.20 | +0.09 |
| | 30/75 | +0.08 | +0.01 | +0.17 | +0.25 |
| | 30/90 | +0.53 | +0.46 | +0.50 | +0.49 |
| | 40/11 | −0.48 | +0.58 | −0.51 | −0.49 |
| | 40/75 | +0.06 | +0.23 | 0.00 | +0.11 |
| | 40/90 | +0.87 | +1.27 | +1.16 | +1.23 |
| β-½H$_2$SO$_4$ | 40/75 | +1.33 | +3.79 | +3.38 | +1.69 |
| α-½H$_2$SO$_4$ | 40/75 | +6.0 | +4.85 | +5.46 | +4.04 |

TABLE 2

| | (T/RH = 40/75) | | | | |
|---|---|---|---|---|---|
| SALT FORM | Day 5 | Week 1 | Week 2 | Week 3 | Week 4 |
| β-HCl | ND | 0 | +0.27 | +0.23 | +0.19 |
| α-HCl | +0.56 | +0.79 | ND | ND | ND |

ND = not determined change was evident. As previously mentioned, the hygroscopicity of the β-form of the hemisulphate salt leads to polymorphic conversion to the α-form and, eventually, to degradation.

No change in DSC profile was apparent for the α-form of the hydrobromide salt in the T=40° C./RH=90% samples, whilst HPLC analysis confirmed its stability under all of the conditions studied.

Table 2 shows hygroscopicity results for the α- and β-forms of the hydrochloride salt, expressed as moisture changes determined by % weight change at T=40° C./RH= 75%.

The β-form was judged to be non-hygroscopic on the basis of both the results displayed in Table 2 and the closely comparable results obtained by KFT analysis at week 4, with no solid state instability being detected. Although only 1 week of incubation was conducted for the α-form in this study, it is clear that it had picked up a significant amount of moisture even by this time-point and that this water uptake was associated with changes in the DSC trace which revealed the transformation of the α-form to the β-form under these conditions.

Compression Studies

Samples (200 mg) were compressed using a bench IR press (Graseby Specac Model 15.011) at 5 tonnes for 1 minute using a 13 mm punch and die set, then assessed for colour change and evidence of melting. Further analysis (DSC and HPLC) was conducted after grinding of the compact using a mortar and pestle.

For the α-form of the hydrobromide salt, no changes to the thermogram in respect of either melting point or enthalpy of fusion, after either compression or grinding, were observed. In addition, there was no evidence of a change in sample appearance or punch filming on compaction.

As previously mentioned, the β-form of the hemisulphate salt undergoes a colour change on compression and also causes punch filming on compaction, whilst the β-form of the hydrochloride salt melts and causes sticking of the disk to the punches during compression, which behaviour is unsurprising given the significantly lower m.p. of the latter. The α-form of the hydrochloride salt did not melt on compaction.

Polymorphic Conversion

DSC was used to determine both the polymorphic conversions of the β-forms of the hydrobromide and hemisulphate salts to their respective α-forms, and also the conversion of the α-form of the hydrochloride salt to its β-form which is believed to be an anhydrate-hydrate transition.

No polymorphic transitions of the α-form of the hydrobromide salt were observed under the conditions investigated.

What is claimed is:

1. A crystalline, β-polymorphic form of a compound of formula (I):

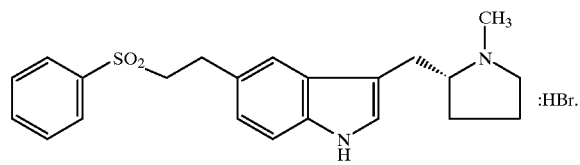

(I)

2. A crystalline, β-polymorphic form of a compound according to claim 1 characterised by an infra-red spectrum as a mull in nujol which shows significant absorption bands at ν=3239, 2672, 2656, 2632, 1409, 1366, 1351, 1334, 1303, 1293, 1152, 1138, 1122, 1098, 1086, 791, 771, 746, 688, 634, 557, 528, 484, 476, 469, 463, 455, 432, 424, 413 and 401 cm$^{-1}$.

3. A compound according to claim 2 which is further characterised by a powder X-ray diffraction pattern obtained using copper radiation filtered with a graphite monochromator (λ=0.15405 nm) which shows main peaks at 11.0, 17.2, 19.2, 20.1, 21.6, 22.6, 23.6 and 24.8 degrees 2θ.

4. A pharmaceutical composition for the treatment of a medical condition for which a selective agonist of 5-HT$_1$ receptors is indicated, comprising an amount of the compound of claim 1 effective in treating such condition and a pharmaceutically acceptable carrier.

5. A pharmaceutical composition for the treatment of a medical condition selected from the group consisting of migraine, cluster headache, chronic paroxysmal hemicrania or headache associated with a vascular disorder, depression, anxiety, an eating disorder, obesity, drug abuse, hypertension and emesis, comprising an amount of the compound of claim 1 effective in treating such condition and a pharmaceutically acceptable carrier.

6. A method of treatment of a human being for a medical condition for which a selective agonist of 5-HT$_1$ receptors is indicated, comprising administering to said human being an amount of a compound according to claim 1 effective in treating such condition.

7. A method for the treatment of a medical condition selected from the group consisting of migraine, cluster headache, chronic paroxysmal hemicrania or headache associated with a vascular disorder, depression, anxiety, an eating disorder, obesity, drug abuse, hypertension, and emesis, comprising administering to said human being an amount of a compound according to claim 1 effective in treating such condition.

8. A process for the preparation of a crystalline, β-polymorphic form of a compound of formula (I):

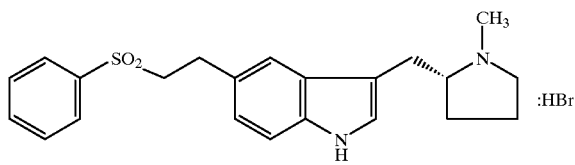

(I)

characterized by an infra-red spectrum as mull in nujol which shows significant absorption bands at v=3239, 2672, 2656, 2632, 1409, 1366, 1351, 1334, 1303, 1293, 1152, 1138, 1122, 1098, 1086, 791, 771, 746, 688, 634, 557, 528, 484, 476, 469, 463, 455, 432, 424, 413, and 401 cm$^{-1}$ which comprises (a) treatment of a solution of a compound of formula (II):

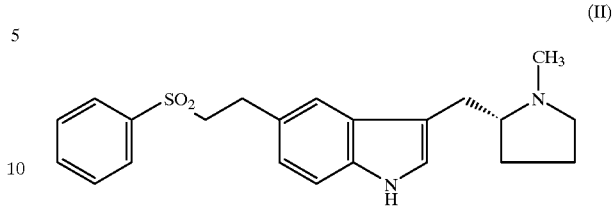

(II)

in a suitable solvent with an aqueous solution of hydrogen bromide and (b) crystallisation from said suitable solvent.

9. A process according to claim 8 wherein the suitable solvent is acetone or an ether solvent such as tetrahydrofuran or 1,2-dimethoxyethane, the aqueous solution of hydrogen bromide is 49% w/w and the treatment therewith is conducted at from 0 to 10° C.

10. A process according to claim 8 wherein the suitable solvent is 1,2-dimethoxyethane.

* * * * *